(12) United States Patent
Zagorchev et al.

(10) Patent No.: US 12,029,575 B2
(45) Date of Patent: Jul. 9, 2024

(54) MESIAL TEMPORAL LOBE EPILEPSY CLASSIFIER BASED ON VOLUME AND SHAPE OF SUBCORTICAL BRAIN REGIONS

(71) Applicant: KONINKLIJKE PHILIPS N.V., Eindhoven (NL)

(72) Inventors: Lyubomir Georgiev Zagorchev, Burlington, MA (US); Miranda Rasmussen, Eugene, OR (US); Shiv Sabesan, Pleasanton, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 759 days.

(21) Appl. No.: 17/279,443

(22) PCT Filed: Sep. 24, 2019

(86) PCT No.: PCT/EP2019/075591
§ 371 (c)(1),
(2) Date: Mar. 24, 2021

(87) PCT Pub. No.: WO2020/064664
PCT Pub. Date: Apr. 2, 2020

(65) Prior Publication Data
US 2022/0031226 A1 Feb. 3, 2022

Related U.S. Application Data

(60) Provisional application No. 62/735,432, filed on Sep. 24, 2018.

(51) Int. Cl.
*A61B 5/00* (2006.01)
*A61B 5/055* (2006.01)
(Continued)

(52) U.S. Cl.
CPC .......... *A61B 5/4094* (2013.01); *A61B 5/0042* (2013.01); *A61B 5/055* (2013.01);
(Continued)

(58) Field of Classification Search
CPC ...... G16H 50/20; G16H 30/40; A61B 5/7275; A61B 5/7267; A61B 5/0042; A61B 5/055;
(Continued)

(56) References Cited

U.S. PATENT DOCUMENTS

2006/0104494 A1   5/2006  Collins et al.
2009/0028403 A1*  1/2009  Bar-Aviv ............. G06T 7/0012
                                                    382/128
(Continued)

FOREIGN PATENT DOCUMENTS

EP    3085305 A1    10/2016
WO    0065985 A2    11/2000

OTHER PUBLICATIONS

Tate, et al., "Volumetric and shape analyses of subcortical structures in United States service members with mild traumatic brain injury", Journal Neurology, Oct. 2016; 263(10), pp. 2065-2079.
(Continued)

*Primary Examiner* — Congvan Tran
(74) *Attorney, Agent, or Firm* — Sherry Austin (57) ABSTRACT

In one embodiment, a method that determine parameters corresponding to shape and volume of the one or more brain structures from the one or more meshes (36) and provides the parameters to a classifier to estimate a probability of a brain abnormality based on the parameters.

14 Claims, 9 Drawing Sheets

(51) Int. Cl.
  *G06T 17/20* (2006.01)
  *G16H 30/40* (2018.01)
  *G16H 50/20* (2018.01)

(52) U.S. Cl.
  CPC .......... *A61B 5/7267* (2013.01); *A61B 5/7275* (2013.01); *G06T 17/205* (2013.01); *G16H 30/40* (2018.01); *G16H 50/20* (2018.01); *G06T 2210/41* (2013.01)

(58) Field of Classification Search
  CPC .. A61B 5/4094; G06T 17/205; G06T 2210/41
  See application file for complete search history.

(56) References Cited

U.S. PATENT DOCUMENTS

| | | | |
|---|---|---|---|
| 2010/0074499 A1* | 3/2010 | Wels | G06T 7/143 382/173 |
| 2013/0259346 A1* | 10/2013 | El-Baz | G06T 7/0012 382/131 |
| 2015/0227702 A1* | 8/2015 | Krishna | A61B 5/7257 705/2 |
| 2016/0166192 A1* | 6/2016 | Lepore | A61B 5/055 600/410 |
| 2016/0306023 A1* | 10/2016 | Zagorchev | G01R 33/4828 |
| 2017/0032520 A1* | 2/2017 | Nitzken | G06T 7/0012 |
| 2018/0344161 A1* | 12/2018 | Meyer | A61B 5/7485 |
| 2019/0059732 A1* | 2/2019 | Kim | A61B 5/0042 |
| 2019/0347795 A1* | 11/2019 | Zagorchev | G16H 30/40 |

OTHER PUBLICATIONS

Memarian, et al., "Quantitative analysis of structural neuroimaging of mesial temporal lobe epilepsy", Imaging Med., Jun. 1, 2013; 5(3), pp. 1-25.

Tardif, et al., "Segmentation of Cortical MS Lesions on MRI Using Automated Laminar Profile Shape Analysis", MICCAI 2010, Part III, LNCS 6363, pp. 181-188.

Jamea, et al., "Volumetric and Shape Analysis of the Subcortical Regions in Schizophrenia Patients: A Pilot Study", Journal of Clinical Imaging Science, vol. 9, Jan. 31, 2019, pp. 1-5.

Rudie, et al., "Machine learning classification of mesial temporal sclerosis inepilepsy patients", Epilepsy Research 117 (2015) pp. 63-69.

Weese, et al., "Shape Constrained Deformable Models for 3D Medical Image Segmentation", Electronic Publishing, Artistic Imaging and Digital Typography, vol. 2082, Jun. 18, 2001, pp. 380-387.

Hosseini, et al., "Support Vector Machine with Nonlinear-Kernel Optimization for Lateralization of Epileptogenic Hippocampus in MR Images", 2014 36th Annual International Conference of the IEEE Engineering in Medicine and Biology Society, Aug. 26, 2014, pp. 1047-1050.

Zagorchev, et al., "Evaluation of Traumatic Brain Injury Patients Using a Shape-Constrained Deformable Model", Sep. 18, 2011, International Conference on Financial Cryptography and Data Security, pp. 118-125.

Mahmoudi, et al., "Data mining MR image features of select structures for laterization of mesial temporal lobe epilepsy" Plos One, vol. 13, No. 8, Aug. 1, 2018, pp. 1-19.

Cantor-Rivera, et al., "Detection of temporal lobe epilepsy using support vector machines in multi-parametric quantitative MRI Imaging", Computerized Medical Imaging and Graphics, vol. 41, Apr. 1, 2015, pp. 14-28.

Esmaeilzadeh, et al., "Mesial Temporal Lobe Epilepsy Lateralization Using SPHARM-Based Features of Hippocampus and SVM", Proceedings of SPIE, vol. 8314, Feb. 10, 2012, pp. 83144H-1 to 83144H-10.

Wenzel, et al., "Rapid fully automatic segmentation of subcortical brain structures by shape-constrained surface adaptation", Medical Image Analysis, Oxford University Press, vol. 46, Mar. 9, 2018, pp. 146-161.

International Search and Written Opinion for International Application No. PCT/EP2019/075591, filed Sep. 24, 2019, 7 pages.

* cited by examiner

MESIAL TEMPORAL LOBE EPILEPSY CLASSIFIER BASED ON VOLUME AND SHAPE OF SUBCORTICAL BRAIN REGIONS

RELATED APPLICATIONS

This application is the U.S. National Phase application under 35 U.S.C. § 371 of International Application No. PCT/EP2019/075591, filed on Sep. 24, 2019, which claims the benefit and priority to Provisional Application No. 62/735,432, filed Sep. 24, 2018, which is incorporated by referenced in its entirety.

FIELD OF THE INVENTION

The present invention is generally related to detection of brain abnormalities.

BACKGROUND OF THE INVENTION

Epilepsy is a public health problem that affects almost 3 million individuals in the US alone. By age 75, 3% of the population will develop epilepsy and 10% of the population will have had at least one seizure. The most common form of medically intractable epilepsy is mesial temporal lobe epilepsy (MTLE), which is usually related to mesial temporal sclerosis (MTS). In those cases, if a seizure focus can be localized, surgery to remove the seizure focus can be curative. Common pathological findings in patients with MTS include atrophy of brain structures in the mesial temporal lobe, primarily the hippocampus and amygdala, and also the entorhinal cortex.

Qualitative visual assessment of subtle structural abnormalities is difficult and subjective even for experienced neuro radiologists. Quantitative MRI techniques that can improve the standard visual inspection have been developed. Hippocampal volume from structural MRI can be helpful in lateralization of temporal lobe epilepsy (TLE). Proposed approaches rely on absolute hippocampal volumes and values relative to total intracranial volumes. Hippocampal asymmetry has been used as an alternative measure to detect and assess the effect of TLE. Although ipsilateral hippocampal atrophy and contralaterally normal hippocampal volumes have been associated with TLE, previous work suggests that bilateral hippocampal atrophy is also present in TLE patients.

Mesial temporal lobe epilepsy (MTLE) is the most common focal form of epilepsy in adults. Surgery can be curative if a seizure focus can be localized. However, there are many patients with seizures for whom qualitative magnetic resonance imaging (MRI) is non-revealing. A methodology capable of detecting subtle structural abnormalities might prove helpful in identifying affected individuals and pinpointing abnormal brain regions in which the seizure focus is embedded. Volumetric analysis of MR data has been described as superior to subjective qualitative review, but it is not commonly used in routine clinical practice.

While automated methods to detect visually apparent abnormalities in the mesial temporal lobe (MTL) are useful in overcoming human interpretive errors, there may be an even greater benefit in detecting MTL abnormalities that are not visible to an experienced image interpreter. Unlike patients with clear evidence of MTS, surgical candidates with a suspicion of MTLE who have a non-lesional MRI typically undergo intracranial EEG monitoring, an invasive test which involves some risk to the patient and significant expense, prior to potential curative surgery. If MTS could be detected by other means in these qualitatively non-lesional MRIs, the need for further invasive testing could be obviated.

SUMMARY OF THE INVENTION

One object of the present invention is to detect a brain abnormality even when imaging fails to present a clear visualization of the brain abnormality. To better address such concerns, in a first aspect of the invention, a method is disclosed that determines features/parameters corresponding to shape and volume of the one or more brain structures from the one or more meshes and provides the parameters to a classifier to estimate a probability of a brain abnormality based on the parameters. Through this approach, risky invasive procedures to confirm whether there is a brain abnormality may be obviated.

In one embodiment, the method receives one or more meshes corresponding to a limbic system and basal ganglia of the brain. By doing so, the method hones in on structures within which atrophy may provide an important indicator of a brain abnormality such as medial temporal lobe epilepsy.

In one embodiment, the method receives one or more meshes corresponding to one or any combination of a hippocampus, amygdala, globus pallidus, lateral ventricle, putamen, thalamus, caudate, and nucleus accumbens. The importance of these structures to medial temporal lobe epilepsy assessment enables an efficient and effective estimate of the probability.

In one embodiment, the parameters are determined by measuring the volume; computing three principle inertias, a sphericity index, a surface area of a convex hull, an inverse value of the surface area; and determining bilateral asymmetry indices and asymmetry in dominant inertias to provide objective metrics in the determination of atrophy among subcortical and/or cortical structures.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Disclosed herein are certain embodiments of a mesial temporal lobe epilepsy (MTLE) preprocessor and classifier and corresponding systems and methods that combine volumetric and shape analysis of subcortical brain regions (and in some embodiments, cortical brain regions) in a supervised machine learning approach in an attempt to discover differentiating patterns in the data. In some embodiments, the MTLE preprocessor and classifier makes use of a shape-constrained, deformable brain model that enables rapid and accurate quantitative analysis capable of differentiating magnetic resonance (MR) images of subjects with MTLE, including cases that were qualitatively interpreted as non-lesional, from healthy controls.

Digressing briefly, and as indicated above, abnormalities or lesions in the mesial temporal lobe caused by epilepsy may sometimes be difficult to detect in an MR image, either visually or with existing automated methods. Subjects with suspected MTLE who have a non-lesional MR image typically undergo intracranial, electroencephalogram (EEG) monitoring, which is risky, expensive and invasive. Certain embodiments of an MTLE preprocessor and classifier may be used to detect MTLE, particularly in these non-lesional MR imaging scenarios, obviating the need for further invasive testing.

Having summarized certain features of an MTLE preprocessor and classifier of the present disclosure, reference will now be made in detail to the description of an MTLE preprocessor and classifier as illustrated in the drawings. While an MTLE preprocessor and classifier will be described in connection with these drawings, there is no intent to limit it to the embodiment or embodiments disclosed herein. For instance, though emphasis is placed on brain abnormalities associated with MTLE, it should be appreciated that the methods associated with an embodiment of an MTLE preprocessor and classifier may be modified to detect other brain or organ abnormalities through the use of models, and hence are also contemplated to be within the scope of the disclosure. Also, though focus of the description is on the use of sub-cortical brain structures, in some embodiments, both cortical and sub-cortical brain structures may be used in some embodiments. Further, although the description identifies or describes specifics of one or more embodiments, such specifics are not necessarily part of every embodiment, nor are all of any various stated advantages necessarily associated with a single embodiment. On the contrary, the intent is to cover all alternatives, modifications and equivalents included within the principles and scope of the disclosure as defined by the appended claims. For instance, two or more embodiments may be interchanged or combined in any combination. Further, it should be appreciated in the context of the present disclosure that the claims are not necessarily limited to the particular embodiments set out in the description.

Figure 1:
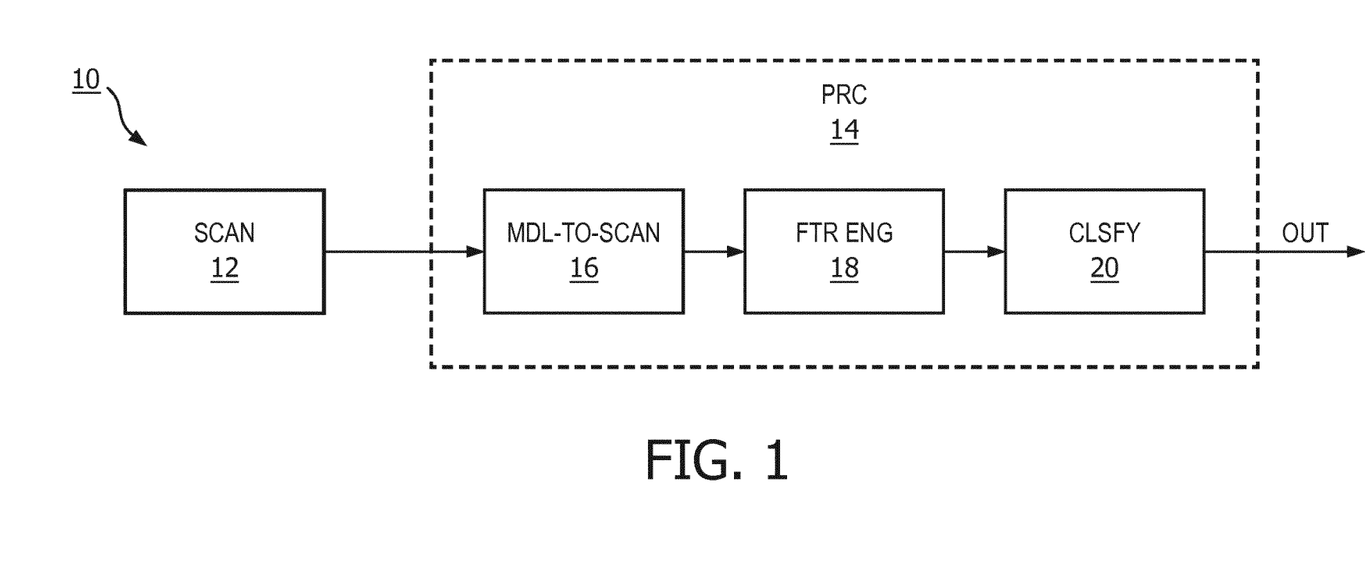
FIG. 1 is a block diagram that illustrates a system for estimating a probability of mesial temporal lobe epilepsy (MTLE), in accordance with an embodiment of the invention.

Referring now to FIG. 1, shown is an embodiment of an MTLE preprocessor and classifier system 10 that estimates a probability of MTLE. It should be appreciated by one having ordinary skill in the art in the context of the present disclosure that the MTLE preprocessor and classifier system 10 is one example among many, and that some embodiments of an MTLE preprocessor and classifier system 10 may have fewer, greater, and/or different functionality than that depicted in FIG. 1. For instance, the MTLE preprocessor and classifier system 10 may comprise all of the functionality depicted in FIG. 1 in one embodiment, or a subset of the depicted functionality in some embodiments. The MTLE preprocessor and classifier system 10 comprises a magnetic resonance imaging (MRI) or scan system (SCAN) 12 and a processing system (PRC) 14, which includes a model-to-scan module (MDL-TO-SCAN) 16 configured to adapt a shape deformable brain model to each new scan received from the scan system 12, a feature engineering module (FTR ENG) 18 configured to perform feature engineering on sub-cortical (and in some embodiments, cortical) structures of the brain model, and one or more classifiers (CLSFY) 20 configured to estimate a probability of a brain abnormality (e.g., in this case, MTLE) in a subject based on training of each classifier on various groups of subjects/conditions, as explained further below. Note that a module (and the classifier 20) as used herein may include hardware, software/firmware/microcode (generally, referred to as software), or a combination of hardware and software.

The scan system 12 may comprise a magnetic resonance imaging scanner (e.g., 1.5T, 3T, etc.), which generally includes a main magnet of superconducting, resistive, permanent, or other magnetic types, gradient (x, y and/or z) coils and/or shim coils, and an RF coil. The main magnet produces a substantially homogeneous, temporally constant main magnetic field $B_0$ in an examination region within which a subject is situated. Various controls (e.g., computer keyboard or other interfaces, such as a console) may be used to enable adjustment of operations of the scanner, including to modify gradient direction and/or magnetic field homogeneity, enable volume of interest placement and/or shimming, among other operations. The scan system 12 further comprises an MR reconstructor and a data repository, which may be co-located with the scanner or remotely accessed (e.g., over one or more networks). The MR reconstructor comprises a computational device or devices that are configured to reconstruct the MR signals and generates MRI image data, and the data repository is configured to store the image data generated by the scanner. In some embodiments, the data repository may comprise a picture archiving and communication system (PACS), a radiology information system (RIS), a hospital information system (HIS), an electronic medical record (EMR) database, a server, a computer, and/or other data repository. In some embodiments, the scan system 12 may be co-located with the processing system 14, and in some embodiments, the scan system 12 may be coupled to the processing system 14 over one or more networks, including a wide area network (WAN), metropolitan area network (MAN), or one or more local area networks (LANs). In some embodiments, the scan system may include additional or other imaging modalities.

The processing system 14 receives the image data for each patient from the scan system 12. In particular, the model-to-scan module 16 is configured to apply an automatic shape-constrained deformable brain model (see FIG. 3B) to MRI scans to segment a set of sub-cortical brain regions. The model consists of a set of triangular meshes that provide point-based correspondence from one subject to another. The adaptation of the model to a new scan (see FIG. 3C) is rapid and fully automatic. The process of adaptation is described further below in association with FIGS. 3A-3C.

The feature engineering module 18 is configured to extract quantitative shape features and volume measurements (also referred to as parameters, where features and parameters are used interchangeably herein) from subcortical meshes included in the brain model. These computations may be performed for each mesh. Further description of this process is described below in association with FIG. 4.

The classifier(s) 20 comprises a machine learning model (e.g., support vector machine) that is trained and subsequently used to classify each new subject based on the quantitative features evaluated (preprocessed) in the feature engineering module 18. That is, the classifier 20 receives as input the quantitative features/parameters of the brain model and outputs an estimate or probability of MTLE or related metrics (e.g., laterality) for each subject. Though a support vector machine is illustrative of one example machine learning model employed by the classifier 20, other machine learning techniques may be employed, including logistic regression, random forest, neural networks (e.g., recurrent neural networks, spiking neural networks, capsule networks), rules-based approaches, Bayesian/statistical methods, xgboost, or other pattern recognition algorithms.

Note that the different functionality of the processing system 14 (e.g., the model-to-scan module 16, feature engineering module 18, classifier 20) may be co-located in a single device, or distributed among multiple devices in a same location or distributed among one or more networks. For instance, in some embodiments, one or more functionality of the processing system 14 may be implemented in a cloud computing environment. When embodied as a cloud service or services, the cloud computing environment may comprise an internal cloud, an external cloud, a private cloud, or a public cloud (e.g., commercial cloud). For instance, a private cloud may be implemented using a variety of cloud systems including, for example, *Eucalyptus* Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). In some embodiments, the one or more functionality of the processing system 14 may be configured into multiple, logically-grouped servers (run on server devices), referred to as a server farm. The server devices may be geographically dispersed, administered as a single entity, or distributed among a plurality of server farms. The server devices may be logically grouped as a farm that may be interconnected using a wide-area network (WAN) connection or medium-area network (MAN) connection. The server devices may each be referred to as, and operate according to, a file server device, application server device, web server device, proxy server device, and/or gateway server device.

Cooperation with the processing system 14 may be facilitated (or enabled) through the use of one or more application programming interfaces (APIs) that may define one or more parameters that are passed between a calling application and other software code such as an operating system, library routine, and/or function that provides a service, that provides data, or that performs an operation or a computation. The API may be implemented as one or more calls in program code that send or receive one or more parameters through a parameter list or other structure based on a call convention defined in an API specification document. A parameter (i.e., in the context of an API, not feature engineering) may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

Figure 2A:
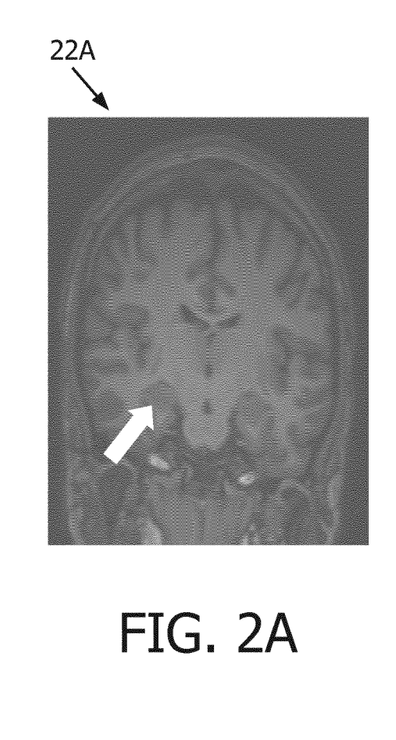
FIGS. 2A-2C are schematic representations of images for a brain of subjects with normal, MTLE with no visual indication of MTLE, and MTLE with a visual indication, in accordance with an embodiment of the invention.
Figure 2B:
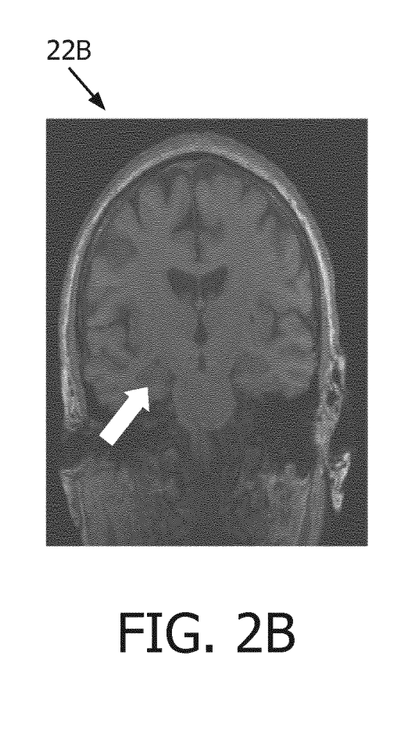
Figure 2C:
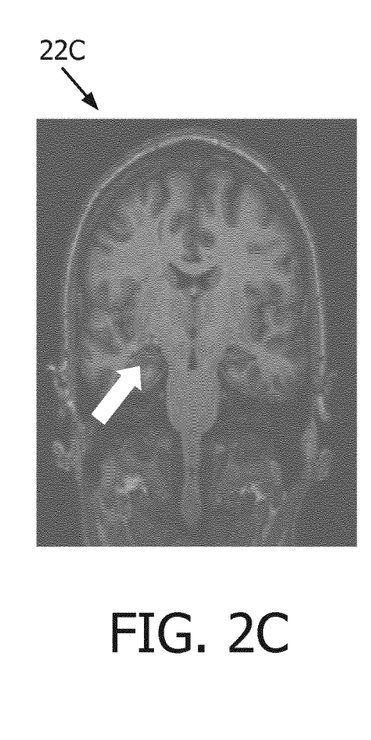

Referring now to FIGS. 2A-2C, shown are schematic representations of images (coronal cross sections) of a brain of subjects with normal (image 22A of FIG. 2A), MTLE with no visual indication of MTLE (image 22B of FIG. 2B, also referred to as MTLE NL), and MTLE with a visual indication (image 22C of FIG. 2C, also referred to as MTLE+). The arrow overlaid onto each of the images 22A-22C points to the hippocampus as an example subcortical structure, and as shown, reveals no visually perceived abnormalities in the normal 22A and MTLE NL 22B images of FIGS. 2A-2B, but a subtle indication of atrophy is perceptible in the MTLE+ image of FIG. 2C. The atrophy may manifest itself in a normally symmetrical or somewhat symmetrical structure becoming asymmetrical (e.g., a structure with a normally ellipse-like outline now having more of a figure-eight outline, for instance). Certain embodiments of an MTLE preprocessor and classifier can assist in the analysis of MTLE for each case (normal, MTLE NL, MTLE+), among others, providing a verification or higher confidence of diagnosis and/or the avoidance of risky procedures (e.g., in the case of MTLE+).

FIGS. 2A-2C are also representative of some types of groups that may be used to train classifier models. As is known, supervised machine learning refers to a process of a model or algorithm learning from a training dataset. For input variables (x) and an output variable (Y), an algorithm is used to learn a mapping function from the input to the output (e.g., Y=f(X)). One goal is to approximate the mapping function so well that output variables (Y) may be predicted with every new input data (X). Stated otherwise, knowing the correct answers, the algorithm iteratively makes predictions on the training data and is corrected throughout the learning process. Learning stops when the algorithm achieves an acceptable level of performance, which may be achieved through one of various validation strategies (e.g., leave-one-out cross validation) and through the use of various performance measure, such as receiver operating characteristic (ROC) measures. Thus, one approach to classifier training is to use groups of subjects of various categories, including healthy controls of a similar age and gender distribution as MTLE subjects (e.g., FIG. 2A), subjects with mesial temporal sclerosis having visibly normal MRIs (e.g., FIG. 2B) and subjects with mesial temporal sclerosis visibly perceived on the MRIs (e.g., FIG. 2C), with the evaluation/diagnosis of MTLE achieved by a team of experts, clinicians, etc. That is, groups may be defined according to normal, MTLE NL, and MTLE+ groups corresponding to laterality issues, such as MTLE+ Left hemisphere, MTLE+ Right hemisphere, among other group categorizations. Then, the processing performed according to the processing circuit 14 (e.g., via the model-to-scan module 16 and feature engineering module 18) is used to train one or more classifiers. That is, training is implemented in the model-to-scan module 16 and feature engineering module 18 in similar manner as performed during implementation for each new scan. One particular difference is in the normalization of data preceding the classifier 20 during training, which in some embodiments, is not implemented in the implementation stage. Further discussion of normalization is provided below in association with FIG. 4.

The classifier(s) 20 may be implemented according to a two-stage classification approach that may be used to first confirm MTLE, even in subjects with non-lesional MRI, and then assess the level of severity and laterality. In some embodiments, the classifier(s) 20 may be trained to permit comparison of obtained results to clinical reads and/or additional data analysis, to differentiate healthy controls from MTLE MRI NL and MTLE MRI+ subjects based on quantitative parameters/features derived from volume and shape of subcortical brain regions (feature engineering), to predict laterality of MTLE based on quantitative features derived from a data set containing MTLE MRI+ Left and MTLE MRI+ Right subjects, and/or to establish MTLE disease biomarkers based on quantitative features derived from the limbic system combined with the basal ganglia, including the hippocampus, amygdala, thalamus, caudate, putamen, and globus pallidus. In some embodiments, training may include the use of other imaging and/or diagnostic modalities, including the use of genetics analysis, resulting in a multi-modal classifier(s).

Figure 3A:
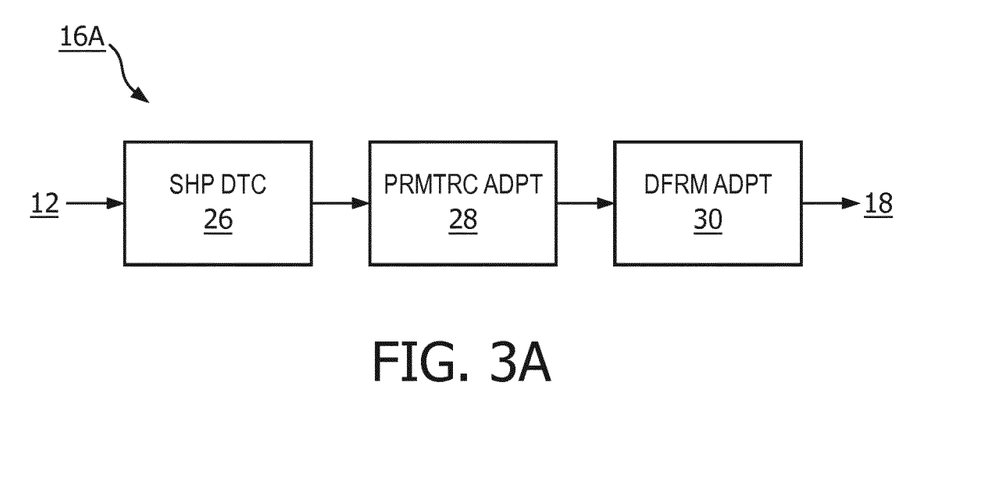
FIG. 3A is a block diagram that illustrates an example method of adapting a shape-constrained, deformable brain model to an imaging scan of a subject, in accordance with an embodiment of the invention.
Figure 3B:
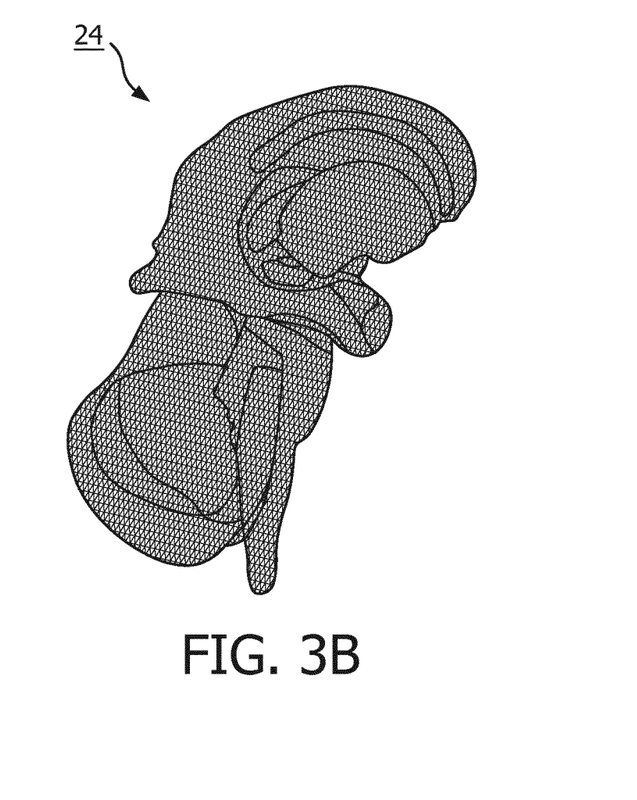
FIG. 3B is a schematic representation of an example shape-constrained, deformable brain model, in accordance with an embodiment of the invention.
Figure 3C:
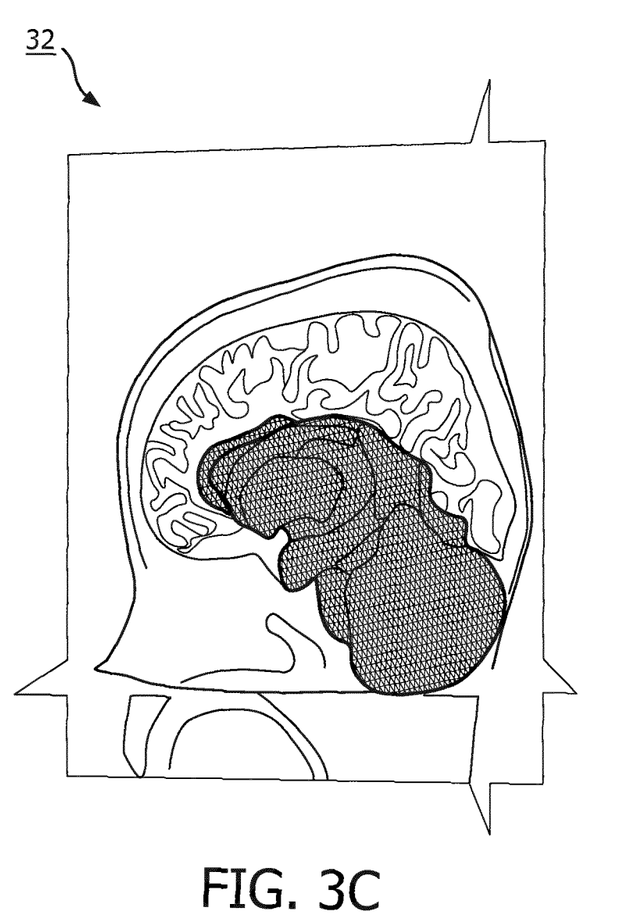
FIG. 3C is a schematic representation of an example shape-constrained, deformable brain model adapted to a scan of a subject, in accordance with an embodiment of the invention.

Attention is directed to FIG. 3A, which illustrates an example method 16A of the model-to-scan module 16 of FIG. 1, which is configured to adapt a shape-constrained, deformable brain model 24 (FIG. 3B) to an imaging scan of a subject (result shown in FIG. 3C). With reference to FIGS. 3A-3C, the method 16A (e.g., the model-to-scan module 16) receives MRI image data from the scan system 12 and accesses (e.g., from a model bank of different brain models (e.g., pediatric, adult, etc.) in local or remote storage) the brain model 24 (or in some implementations, any anatomical model of interest). The brain model 24 comprises a shape-constrained deformable brain model, which in this example consists of a set of triangular meshes that represent subcortical brain structures. Examples of suitable brain models are described in L. Zagorchev, A. Goshtasby, K. Paulsen, T. McAllister, S. Young, and J. Weese, Manual annotation, 3-D shape reconstruction, and traumatic brain injury analysis, Int'l Workshop Multimodal Brain Image Analysis (MBIA), Toronto, Calif., September 2011, and L. Zagorchev, C. Meyer, T. Stehle, R. Kneser, S. Young, and J. Weese, Evaluation of Traumatic Brain Injury patients using a shape-constrained deformable model, Int'l Workshop Multimodal Brain Image Analysis (MBIA), Toronto, Calif., September 2011. Other models are also contemplated herein. The method 16A segments the brain structures represented in the MRI image data based on the anatomy represented in the brain model 24. In one non-limiting example, this generally includes performing an initial registration between the brain model 24 and the MRI image data, transforming the brain model 24 to the anatomy in the MRI image data based on a transform (e.g., the Hough transform), performing a parametric adaptation of the brain model 24 (e.g., pose and/or piecewise), and performing a deformable adaptation of the brain model 24.

The adaptation of the model 24 to a new scan is rapid (e.g., approximately 20 seconds on an HP ZBook 15 G2, 8 GB RAM) and fully automatic, and is achieved via a number of image processing steps as shown in FIG. 3A. For instance, in one embodiment, the adaptation to a new image starts with shape detection (SHP DTC) 26 based on the Generalized Hough Transform to identify the approximate position and orientation of the model 24 in the new image. In the next step, global and local parametric transformations (PRMTRC ADPT) 28 are used to adapt the brain model 24 and bring it closer to its target boundaries, which is accomplished by applying a similarity transform to all anatomical brain structures in an iterative approach that consists of boundary detection and adaptation. Then, the same process is repeated locally with a different similarity transform for each brain structure. And finally, when the model 24 is in close proximity to the target structures in the new image, a deformable adaptation step (DFRM ADPT) 30 guided by the minimization of an energy term defined as a weighted sum of external and internal energies is performed. The external energy moves the meshes closer to detected image boundaries, while the internal energy penalizes deviation from an a priori shape geometry derived from manual ground truth tracings and a set of training volumes. The result is the model adapted to the new image scan (meshes), as shown by image 32 of FIG. 3C, which is provided to the feature engineering module 18. Further details about the brain model have been published previously (Weese et al. 20414; Zagorchev et al., 2011, Zagorchev et al. 2016). In some embodiments, other known techniques can alternatively be used.

Figure 4:
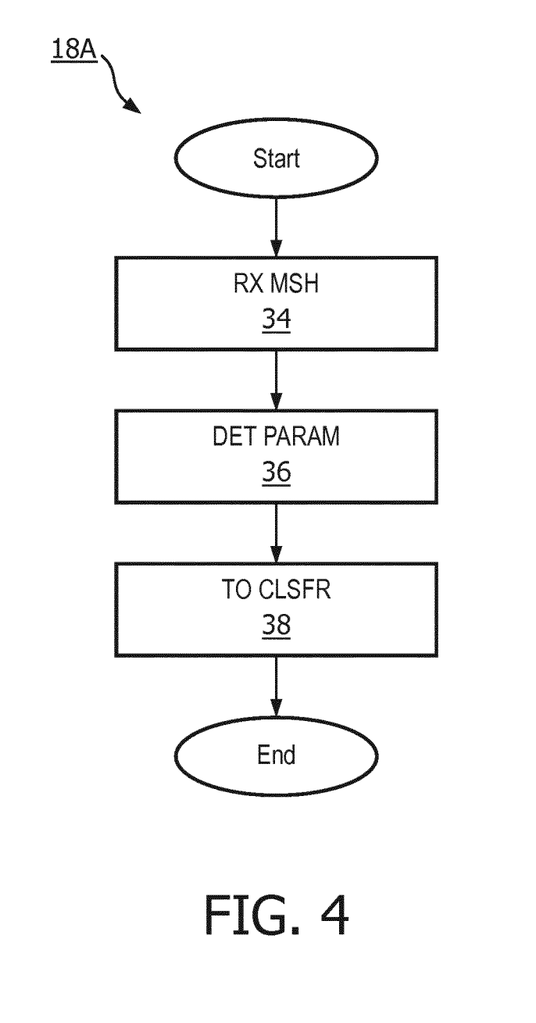
FIG. 4 is a flow diagram that illustrates an example method of feature engineering of a brain model, in accordance with an embodiment of the invention.

Referring now to FIG. 4, shown is an example method 18A of feature engineering of the (adapted) model (e.g., of image 32, FIG. 3C) as implemented by the feature engineering module 18 (FIG. 1). In one embodiment, the method 18A comprises receiving one or more meshes corresponding to one or more structures of a brain (RX MSH) 34, determining parameters (features) corresponding to shape and volume of the one or more brain structures from the one or more meshes (DET PARAM) 36, and providing the parameters to a classifier to estimate a probability of a brain abnormality based on the parameters (TO CLSFR) 38. Explaining further, the feature engineering module 18 receives, as input, the mesh(es) generated from the model-to-scan module 16, as explained above. For the determination of parameters (36), in one embodiment, quantitative shape features may be extracted from sub-cortical meshes (and in some embodiments, cortical meshes) included in the (adapted) brain model, their volume and the following shape parameters computed for each mesh: three principal inertias, a sphericity index, a surface area of the convex hull, and an inverse value of the convex hull surface area. In addition, volumetric measurements, including bilateral asymmetry indices for the hippocampus, amygdala, globus pallidus, lateral ventricle, putamen, thalamus, caudate, and nucleus accumbens can be generated, as well as asymmetry in dominant inertias for the hippocampus and amygdala. The asymmetries may be computed according to the following equation (Eqn. 1):

$$\text{Asymmetry}(V) = (V_L - V_R)/(V_L + V_R), \quad \text{Eqn. 1}$$

where $V_L$ and $V_R$ are the volumes of structure (V) from the left and right cerebral hemispheres, respectively. In total that creates 121 features (16 brain structures×7 (volume+6 shape parameters)+9 asymmetries) for each brain scan/subject. In some embodiments, other quantities of features may be used. It is noted that the point based correspondence provided by the (adapted) brain model provides a unique and reproducible shape encoding. In (38), this information is provided to the classifier 20 (FIG. 1).

Classification of new subjects may be performed based on the quantitative features described above.

Digressing briefly, it is noted that, with regard to the training of classifier(s), before performing classification, all features in the training are normalized by subtracting the mean and dividing by their standard deviation. Mean and standard deviations may be obtained using, in some embodiments, only the training set to avoid data leakage. In some embodiments, normalization may be performed when implementing the trained classifiers on new data. In addition, the means of asymmetry features for all normal subjects in the training set may be obtained and used to normalize all asymmetry features according to the following equation (Eqn. 2):

$$\text{abs\_asymmetry}(V) = |\text{asymmetry}(V) - \overline{\text{asymmetry}(V)}|, \quad \text{(Eqn. 2)}$$

where $\overline{\text{asymmetry}(V)}$ is the mean of asymmetry features for normal subjects in the training set. The abs_asymmetry (V) provides a measure of deviation in asymmetry from the mean asymmetry of normal subjects.

Figure 5A:
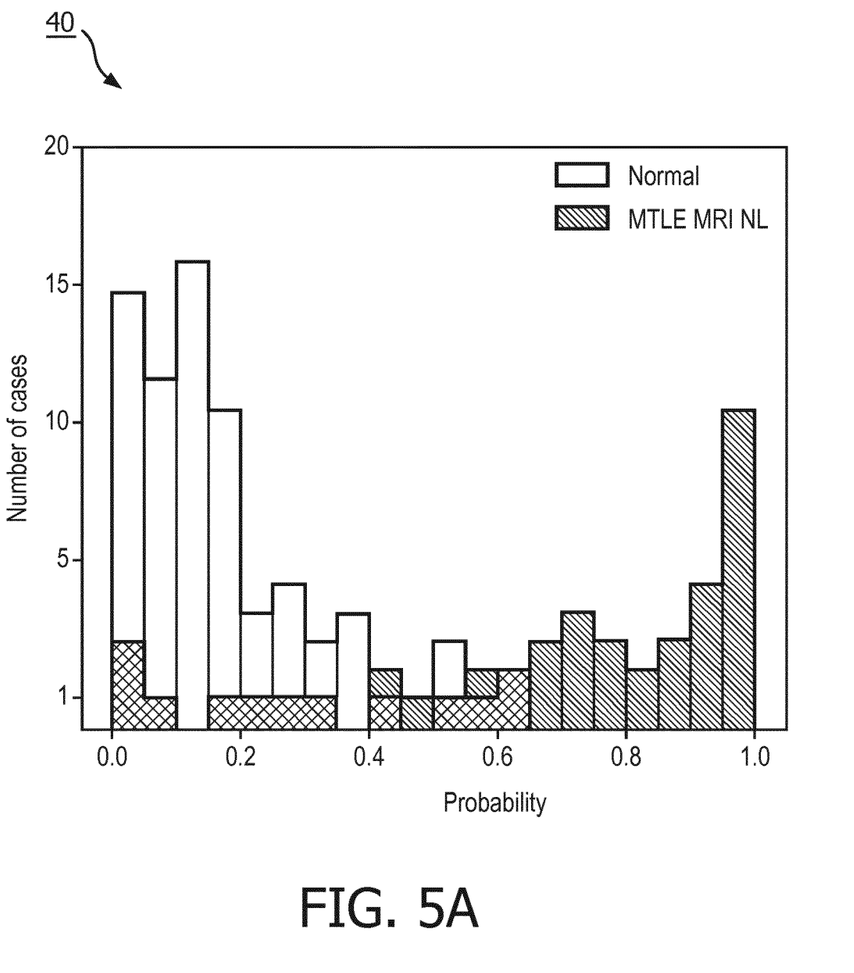
FIGS. 5A-5B are plot diagrams that illustrate example performances of classifiers that distinguish between normal and MTLE subjects, in accordance with an embodiment of the invention.
Figure 5B:
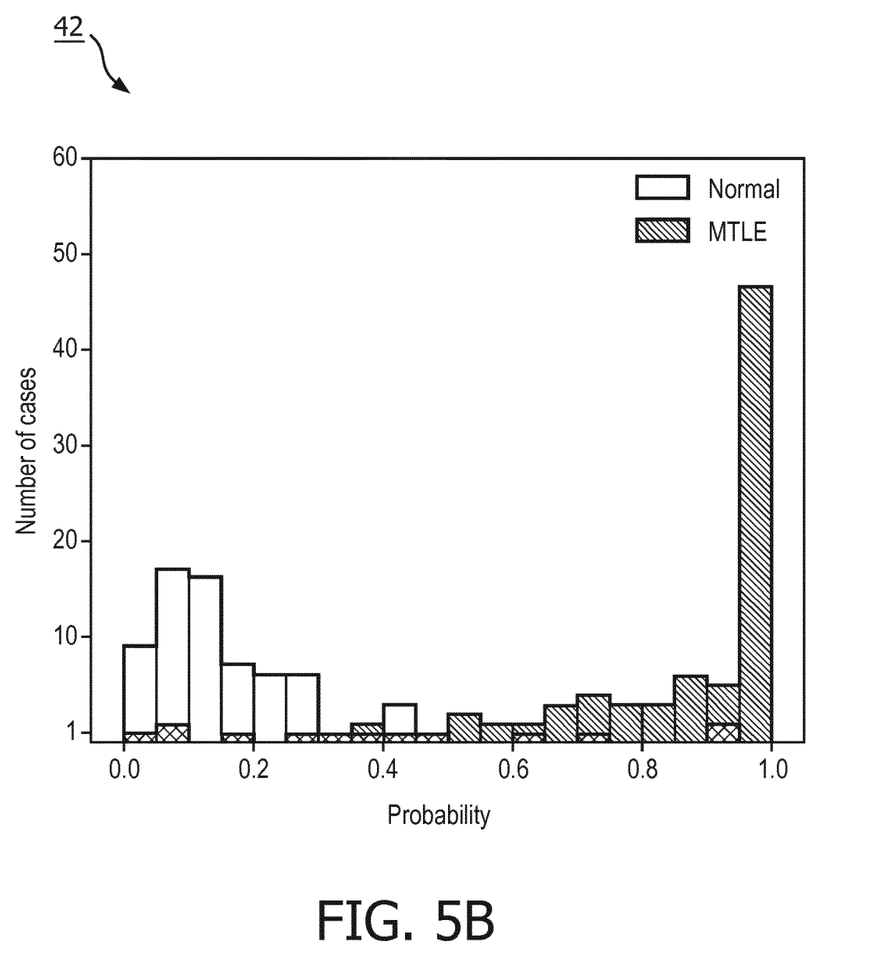

The classifier 20 (FIG. 1) may be implemented to perform classification and estimate probability. The area under the curve (AUC) for receiver operating characteristic (ROC) may be used as an indicator of the performance of the classifier 20. Different classifiers may be trained in an attempt to classify normal vs. MTLE MRI NL, normal vs. MTLE MRI+, and to determine the laterality of MTLE, as shown respectively in plot diagrams 40 (FIG. 5A) and 42 (FIG. 5B). Other comparisons may be achieved through training.

Figure 6:
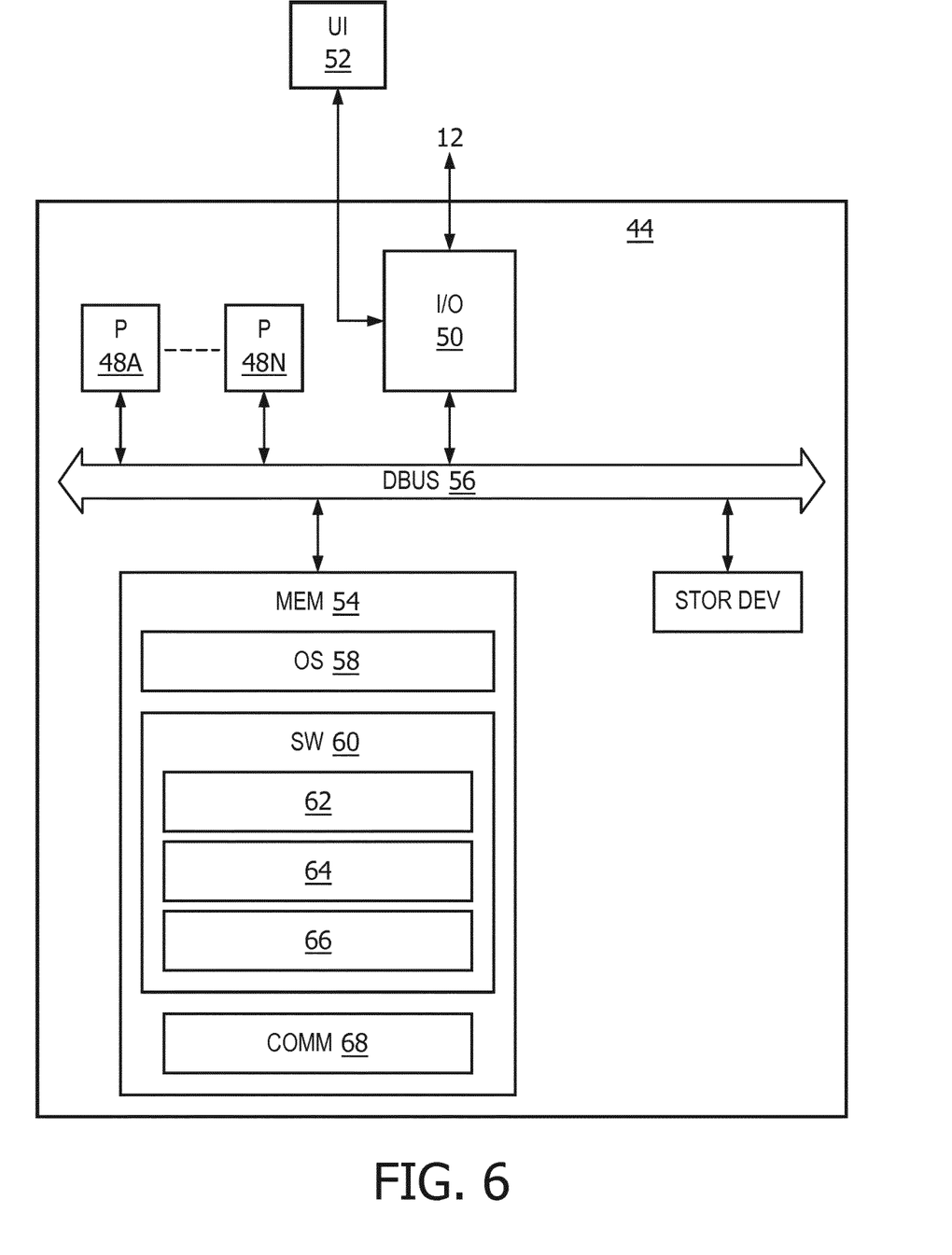
FIG. 6 is a block diagram that illustrates an example system that estimates a probability of an MTLE condition of a subject using shape and volume features/parameters determined from a brain model, in accordance with an embodiment of the invention.

Having described certain embodiments of an MTLE preprocessor and classifier, attention is directed to FIG. 6, which illustrates yet another embodiment of an example MTLE preprocessor and classifier 44 that is configured to estimate a probability of an MTLE condition of a subject using shape and volume parameters determined from a brain model. In the depicted embodiment, functionality of the MTLE preprocessor and classifier 44 is implemented as a system of co-located software and hardware components collectively embodied as a computing device (which may include a medical device). It should be appreciated that, in some embodiments, functionality of the MTLE preprocessor and classifier 44 may be implemented via plural computing devices that are networked at a similar location or situated in remotely different locations and connected via one or more networks. Hereinafter, the MTLE preprocessor and classifier 44 and computing device are used interchangeably (and referenced by reference number 44). One having ordinary skill in the art should appreciate in the context of the present disclosure that the example computing device 44 is merely illustrative of one embodiment, and that some embodiments of computing devices may comprise fewer or additional components, and/or some of the functionality associated with the various components depicted in FIG. 6 may be combined, or further distributed among additional modules or computing devices, in some embodiments. It should be appreciated that certain well-known components of computer systems are omitted here to avoid obfuscating relevant features of the computing device 44.

In one embodiment, the computing device 44 comprises one or more processors (P) 48 (e.g., 48A . . . 48N), input/output (I/O) interface(s) 50 (I/O), one or more user interfaces (UI) 52, which may include one or more of a keyboard, mouse, microphone, speaker, etc.), and memory 54 (MEM), all coupled to one or more data busses, such as data bus 56 (DBUS). In some embodiments, the user interfaces may be coupled directly to the data bus 56. The memory 54 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 54 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 56 or as a network-connected device (or devices) via the I/O interfaces 50 and one or more networks. In the depicted embodiment, the computing device 44 is coupled to the scan system 12 via the I/O interfaces, though it should be appreciated that the connection may be achieved via one or more networks in some embodiments. The storage device may be embodied as persistent memory (e.g., optical, magnetic, and/or semiconductor memory and associated drives), and in some embodiments, may be used to store data depicted as stored in storage device 20 (FIG. 1). In some embodiments, the storage device or memory 54 may store a model bank, scans, among other subject information.

In the embodiment depicted in FIG. 6, the memory 54 comprises an operating system 58 (OS) (e.g., LINUX, macOS, Windows, etc.), and processing software (SW) 60, which includes a model-to-scan module 62, feature engineering module 64, and classifier module 66. In some embodiments, there may be fewer or additional modules. The modules are depicted in this example as blocks of instructions (e.g., executable code) in the form of software/firmware, though in some embodiments, functionality of the same may be implemented using microcode or via hardware (e.g., circuitry, including application-specific integrated circuits (ASICs), field programmable gate arrays (FPGAs), vector processors, tensor processing units, etc.). Functionality of the processing software 60, including the model-to-scan module 62, feature engineering module 64, and classifier module 66, are similar to like-functionality described above in association with classifier 20, and methods 16A and 18A in FIGS. 3A-4, and thus discussion of the same is omitted here for brevity. The memory 54 further comprises a communications module (COMM) 68. The communications module 68 comprises software/firmware that is configured to enable the communication of information (via the I/O interfaces 50) among other systems and/or devices, including the scan system 12.

Note that the memory 54 and storage device may each be referred to herein as a non-transitory, computer readable storage medium or the like.

Execution of the processing software 60, including the model-to-scan module 62, feature engineering module 64, and classifier module 66, may be implemented by the one or more processors 48 under the management and/or control of the operating system 58. The processor(s) 48 may be embodied as a custom-made or commercially available processor, including a single or multi-core central processing unit (CPU), tensor processing unit (TPU), graphics processing unit (GPU), vector processing unit (VPU), or an auxiliary processor among several processors, a semiconductor based microprocessor (in the form of a microchip), a macroprocessor, one or more application specific integrated circuits (ASICs), field programmable gate arrays (FPGUs), a plurality of suitably configured digital logic gates, and/or other known electrical configurations comprising discrete elements both individually and in various combinations to coordinate the overall operation of the computing device 44.

The I/O interfaces 50 comprise hardware and/or software to provide one or more interfaces to the scan system 12 or other devices. The I/O interfaces 50 may include a cable and/or cellular modem, and/or establish communications with other devices or systems via an Ethernet connection, hybrid/fiber coaxial (HFC), copper cabling (e.g., digital subscriber line (DSL), asymmetric DSL, etc.), using one or more of various communication protocols (e.g., TCP/IP, UDP, etc.). In general, the I/O interfaces 50, in cooperation with the communications module 68, comprises suitable hardware to enable communication of information via PSTN (Public Switched Telephone Networks), POTS, Integrated Services Digital Network (ISDN), Ethernet, Fiber, DSL/ADSL, Wi-Fi, cellular (e.g., 3G, 4G, 5G, Global System for Mobile Communications (GSM), General Packet Radio Service (GPRS), etc.), Bluetooth, near field communications (NFC), Zigbee, among others, using TCP/IP, UDP, HTTP, DSL. The user interfaces 52 may include a keyboard, mouse, microphone, immersive head set, etc., which enable input and/or output by an administrator or other user. In some embodiments, the user interfaces 52 may cooperate with associated software to enable augmented reality or virtual reality.

When certain embodiments of the computing device 44 are implemented at least in part with software (including firmware), it should be noted that the software (e.g., processing software 60, including the model-to-scan module 62, feature engineering module 64, and classifier module 66) can be stored on a variety of non-transitory computer-readable (storage) medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 44 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), TPUs, GPUs, and/or other accelerators/co-processors, etc.

Figure 7:
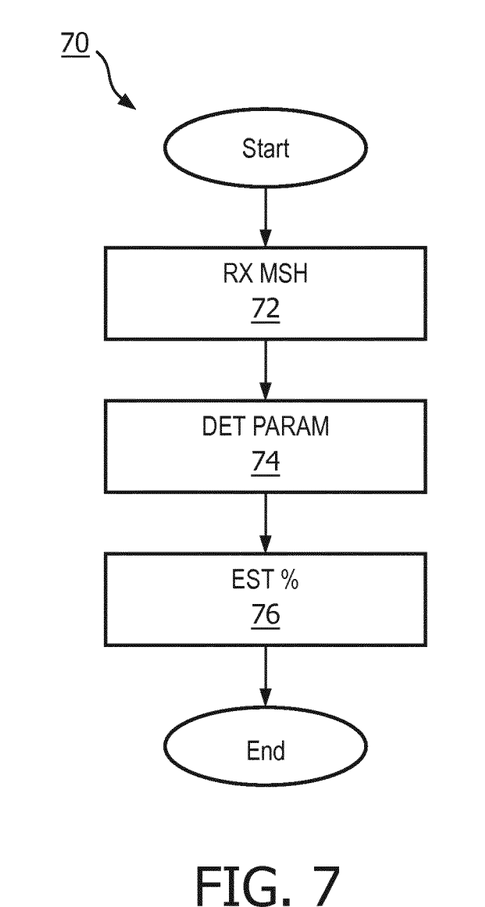
FIG. 7 is a flow diagram that illustrates an example method of estimating a probability of an MTLE condition of a subject using shape and volume parameters determined from a brain model, in accordance with an embodiment of the invention.

Having described certain embodiments of an MTLE preprocessor and classifier, it should be appreciated that an example method of estimating a probability of an MTLE condition of a subject using shape and volume parameters determined from a brain model, depicted in FIG. 7 and denoted as method 70, which is shown bounded by a start and end, comprises receiving one or more meshes corresponding to one or more structures of a brain (RX MSH) 72, determining features/parameters corresponding to shape and volume of the one or more brain structures from the one or more meshes (DET PARAM) 74, and estimating a probability of a brain abnormality based on the parameters (EST %) 76. In some embodiments, the steps 72, 74, and 76 may be implemented by the feature engineering module 64 and classifier module 66. In some embodiments, generation of the adapted model may be implemented by the model-to-scan module 62.

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

Certain embodiments of systems and methods corresponding to an MTLE preprocessor and classifier described herein involve the extraction of shape and volume parameters from a brain model adapted to an MR scan, and automated classification and lateralization of MTLE. Some embodiments of the systems and methods described above have the potential to improve the accuracy of reading of MRI negative data without interfering with time critical clinical workflows. Improved interpretation will lead to better results for clinical decision making as well as better patient outcomes.

In one embodiment, a non-transitory computer readable medium is disclosed comprising instructions that, when executed by one or more processors, causes the one or more processors to: receive one or more meshes corresponding to one or more structures of a brain; determine parameters corresponding to shape and volume of the one or more brain structures from the one or more meshes; and provide the parameters to a classifier to estimate a probability of a brain abnormality based on the parameters.

In one embodiment, the prior non-transitory computer readable medium, wherein the instructions cause the one or more processors to receive one or more meshes corresponding to sub-cortical structures of the brain.

In one embodiment, any one of the prior non-transitory computer readable mediums, wherein the instructions cause the one or more processors to receive one or more meshes corresponding to sub-cortical structures and cortical structures of the brain.

In one embodiment, any one of the prior non-transitory computer readable mediums, wherein the instructions cause the one or more processors to receive one or more meshes corresponding to a limbic system and basal ganglia of the brain.

In one embodiment, any one of the prior non-transitory computer readable mediums, wherein the instructions cause the one or more processors to receive one or more meshes corresponding to one or any combination of a hippocampus, amygdala, globus pallidus, lateral ventricle, putamen, thalamus, caudate, and nucleus accumbens.

In one embodiment, any one of the prior non-transitory computer readable mediums, wherein the one or more meshes each comprise a shape-constrained, deformable brain model that comprises one or more triangular meshes, the one or more meshes adapted to a magnetic resonance imaging scan of a subject.

In one embodiment, any one of the prior non-transitory computer readable mediums, wherein the instructions cause the one or more processors to determine the parameters by: measuring the volume; computing three principle inertias, a sphericity index, a surface area of a convex hull, an inverse value of the surface area; and determining bilateral asymmetry indices and asymmetry in dominant inertias.

In one embodiment, any one of the prior non-transitory computer readable mediums, wherein the instructions further cause the one or more processors to estimate the probability of the brain abnormality.

In one embodiment, any one of the prior non-transitory computer readable mediums, wherein the brain abnormality corresponds to epilepsy.

In one embodiment, a system is disclosed including memory and one or more processors configured to implement the functions for any one of the prior non-transitory computer readable mediums.

In one embodiment, a method is disclosed that implements the functions for any one of the prior non-transitory computer readable mediums.

In one embodiment, a system is disclosed, comprising: a memory comprising instructions; and one or more processors configured by the instructions to: receive one or more meshes corresponding to one or more structures of a brain; determine parameters corresponding to shape and volume of the one or more brain structures from the one or more meshes; and estimate a probability of a brain abnormality based on the parameters.

In one embodiment, the preceding system, wherein the one or more processors are further configured by the instructions to adapt the one or more meshes comprising a shape-constrained, deformable brain model to a magnetic resonance imaging scan of a subject.

In one embodiment, any one of the prior systems, wherein the one or more processors are further configured by the instructions to receive the one or more meshes corresponding to sub-cortical structures of the brain, or sub-cortical structures and cortical structures of the brain.

In one embodiment, any one of the prior systems, wherein the one or more processors are further configured by the instructions to determine the parameters by: measuring the volume; computing three principle inertias, a sphericity index, a surface area of a convex hull, an inverse value of the surface area; and determining bilateral asymmetry indices and asymmetry in dominant inertias.

In one embodiment, any one of the prior systems, wherein the estimate is based on one of a classification of a probability of mesial temporal lobe epilepsy for a subject, a classification of mesial temporal lobe epilepsy of the subject compared to healthy subjects, a classification of mesial temporal lobe epilepsy of the subject compared to subjects with mesial temporal lobe epilepsy and no imaging confirmation, a classification of mesial temporal lobe epilepsy of the subject compared to subjects with mesial temporal lobe epilepsy with imaging confirmation, or laterality of mesial temporal lobe epilepsy of the subject.

In one embodiment, a method implemented by one or more processors is disclosed, the method comprising: at the one or more processors: receiving one or more meshes corresponding to one or more structures of a brain; determining parameters corresponding to shape and volume of the one or more brain structures from the one or more meshes; and estimating a probability of a brain abnormality based on the parameters.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. A non-transitory computer readable medium comprising instructions that, when executed by one or more processors, causes the one or more processors to:

receive a magnetic resonance image scan of a brain of a subject;

access a deformable brain model, the deformable brain model comprising a plurality of meshes;

adapt the deformable brain model to the magnetic resonance image scan of the brain of the subject such that the plurality of meshes are adapted to correspond to one or more structures of the brain of the subject;

determine parameters corresponding to shape and volume of the one or more brain structures from the plurality of meshes; and provide the parameters to a classifier to estimate a probability of a brain abnormality based on the parameters, wherein the classifier is a trained classifier.

2. The non-transitory computer readable medium of claim 1, wherein the plurality of meshes correspond to sub-cortical structures of the brain.

3. The non-transitory computer readable medium of claim 1, wherein the plurality of meshes correspond to sub-cortical structures and cortical structures of the brain.

4. The non-transitory computer readable medium of claim 1, wherein the plurality of meshes correspond to a limbic system and basal ganglia of the brain.

5. The non-transitory computer readable medium of claim 1, wherein the plurality of meshes correspond to one or any combination of a hippocampus, amygdala, globus pallidus, lateral ventricle, putamen, thalamus, caudate, and nucleus accumbens.

6. The non-transitory computer readable medium of claim 1, wherein the plurality of meshes are triangular meshes.

7. The non-transitory computer readable medium of claim 1, wherein the instructions cause the one or more processors to determine the parameters by:
  measuring the volume;
  computing three principle inertias, a sphericity index, a surface area of a convex hull, an inverse value of the surface area; and
  determining bilateral asymmetry indices and asymmetry in dominant inertias.

8. The non-transitory computer readable medium of claim 1, wherein the instructions further cause the one or more processors to estimate the probability of the brain abnormality.

9. The non-transitory computer readable medium of claim 1, wherein the brain abnormality corresponds to epilepsy.

10. The system of claim 1, wherein the plurality of meshes correspond to sub-cortical structures of the brain, or sub-cortical structures and cortical structures of the brain.

11. The system of claim 1, wherein the one or more processors are further configured by the instructions to determine the parameters by:
  measuring the volume;
  computing three principle inertias, a sphericity index, a surface area of a convex hull, an inverse value of the surface area; and
  determining bilateral asymmetry indices and asymmetry in dominant inertias.

12. The system of claim 1, wherein the estimate is based on one of a classification of a probability of mesial temporal lobe epilepsy for a subject, a classification of mesial temporal lobe epilepsy of the subject compared to healthy subjects, a classification of mesial temporal lobe epilepsy of the subject compared to subjects with mesial temporal lobe epilepsy and no imaging confirmation, a classification of mesial temporal lobe epilepsy of the subject compared to subjects with mesial temporal lobe epilepsy with imaging confirmation, or laterality of mesial temporal lobe epilepsy of the subject.

13. A system, comprising:
  a memory comprising instructions; and
  one or more processors configured by the instructions to:
    receive a magnetic resonance image scan of a brain of a subject;
    access a deformable brain model, the deformable brain model comprising a plurality of meshes;
    adapt the deformable brain model to the magnetic resonance image scan of the brain of the subject such that the plurality of meshes are adapted to correspond to one or more structures of the brain of the subject;
    determine parameters corresponding to shape and volume of the one or more brain structures from the plurality of adapted meshes; and
    estimate a probability of a brain abnormality based on the parameters.

14. A method implemented by one or more processors, the method comprising:
  at the one or more processors:
    receiving a magnetic resonance image scan of a brain of a subject;
    accessing a deformable brain model, the deformable brain model comprising a plurality of meshes;
    adapting the deformable brain model to the magnetic resonance image scan of the brain of the subject such that the plurality of meshes are adapted to correspond to one or more structures of the brain;
    determining parameters corresponding to shape and volume of the one or more brain structures from the one or more meshes; and
    estimating a probability of a brain abnormality based on the parameters.

* * * * *